United States Patent [19]

Kato

[11] Patent Number: 5,027,795
[45] Date of Patent: Jul. 2, 1991

[54] MASSAGE MACHINE FOR AUTOMOBILE

[75] Inventor: Kazuhiro Kato, Nishinomiya, Japan

[73] Assignee: Kabushiki Kaisha Kato Haguruma Kogyosho, Osaka, Japan

[21] Appl. No.: 556,505

[22] Filed: Jul. 24, 1990

[30] Foreign Application Priority Data

Aug. 4, 1989 [JP] Japan .................. 1-92483[U]

[51] Int. Cl.$^5$ .......................................... A61H 15/00
[52] U.S. Cl. ........................................ 128/33; 128/32; 128/44; 128/61
[58] Field of Search ................. 128/32, 33, 44, 45, 128/46, 60, 61

[56] References Cited

U.S. PATENT DOCUMENTS

| 4,203,098 | 5/1980 | Muncheryan | 128/33 X |
| 4,258,706 | 3/1981 | Shank | 128/33 |
| 4,354,067 | 10/1982 | Yamada et al. | 128/33 X |
| 4,748,972 | 6/1988 | Hasegawa | 128/33 X |
| 4,750,208 | 6/1988 | Yamada et al. | 128/33 X |

Primary Examiner—Robert A. Hafer
Assistant Examiner—Brian E. Hanlon
Attorney, Agent, or Firm—Armstrong, Nikaido, Marmelstein, Kubovcik & Murray

[57] ABSTRACT

A massage machine for an automobile which comprises a main body suspendaly supported on the back rest of an automobile seat by way of a height-adjustable suspending member, a plurality of ceramic finger pressure balls rotatably borne on the front surface of the main body in a projected state, magnets installed deeply inside of finger pressure ball bearing parts on the front surface of the main body corresponding to each finger pressure ball, attracting and holding each finger pressure ball rotatably about the bearing parts, and bringing about magnetic effects to each finger pressure ball, heater coils disposed at the finger pressure ball bearings parts of the main body correspondng to each finger pressure ball, and connected to an automobile power supply through a power supply outlet such as cigarette lighter, a temperature sensor incorporated in part of the main body to controlling the heater coils to a proper temperature by turning on and off, and a pressure sensor incorporated in part of the main body for controlling the heater coils by turning on and off by sensing the presence or absence of the pushing pressure of the user.

1 Claim, 1 Drawing Sheet

MASSAGE MACHINE FOR AUTOMOBILE

BACKGROUND OF THE INVENTION

1. Field of the Invention

The present invention relates to a massage machine for automobile for healing and eliminating lumbago, stiff shoulder or the like of athlete, professional driver or the like while seated in the driver's seat of automobile.

2. Prior Art

Lumbago, stiff shoulder, etc. are pains for not only athletes and professional drivers, but also for everyone, and an early recovery is desired, but the conventional massage machine is not designed to be used easily in an automobile, it was felt inconvenient for those commutating to the destination by car.

SUMMARY OF THE INVENTION

It is hence a primary object of the invention to present a massage machine excellent in safety and controllability which can be used in a state seated in the driver's seat of an automobile.

To solve the above problems, the invention presents a massage machine for automobile which comprises:
- a main body suspendaly supported on the back rest of an automobile seat by way of a height-adjustable suspending member,
- a plurality of ceramic finger pressure balls rotatably borne on the front surface of the main body in a projected state,
- magnets installed deeply inside of finger pressure ball bearing parts on the front surface of the main body corresponding to each finger pressure ball, attracting and holding each finger pressure ball rotatably about the bearing parts, and bringing about magnetic effects to each finger pressure ball,
- heater coils disposed at the finger pressure ball bearings parts of the main body corresponding to each finger pressure ball, and connected to an automobile power supply through a power supply outlet such as cigarette lighter,
- a temperature sensor incorporated in part of the main body to controlling the heater coils to a proper temperature by turning on and off, and
- a pressure sensor incorporated in part of the main body for controlling the heater coils by turning on and off by sensing the presence or absence of the pushing pressure of the user.

Since the main body is supported suspendably on the back rest of an automobile seat, it is easily detachable, and it can be removed when not necessary, for example, early in the morning when the physical condition is good. When using, for example, in the evening, it can be hooked on the back rest of the seat through the suspending member, and its height can be freely adjusted depending on the painful spots in the shoulder, back or waist.

When the user presses the ailing spot in a specific position toward the main body which is suspended and supported on the back rest of the seat, or presses while slightly changing the position vertically and laterally, the heater coil is turned on through the pressure sensor. The finger pressure balls gradually rise in temperature, and the fatigued muscles are heated and massaged by simultaneously applying the thermomassaging action and finger pressure action for heating and stretching the fatigued and contracted muscles in the ailing spot of the user, and furthermore the magnetic effect by magnets acts on the human body through finger pressure balls to promote the blood circulation, and the muscular fatigue of the ailing spot may be recovered early by these synergistic effects.

Since the finger pressure balls are rotatably borne on the main body, the finger pressure position may be smoothly changed while pressing the body.

The temperature sensor appropriately maintains the temperature of the finger pressure balls, and the pressure sensor automatically cuts off the energization of the heater coil when alighting from the car, and fire is prevented, so that it is quite safe and economical.

DETAILED DESCRIPTION OF THE INVENTION

Figure 1:
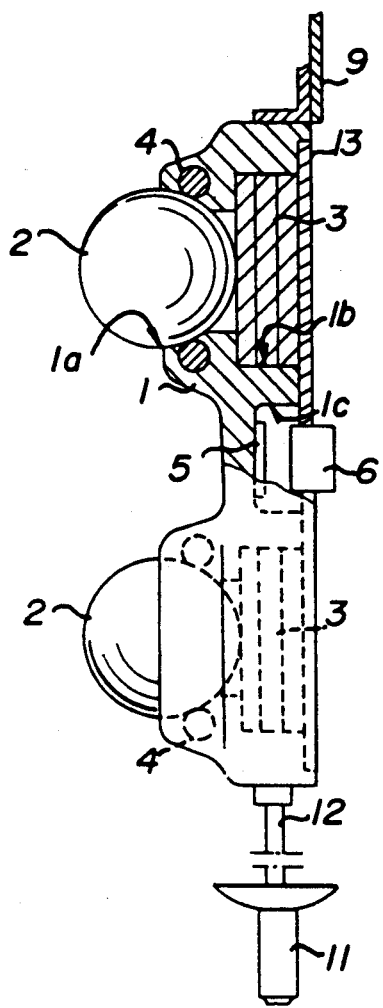
FIG. 1 is a partially cut-away side view showing an embodiment of a massage machine of the invention.
Figure 2:
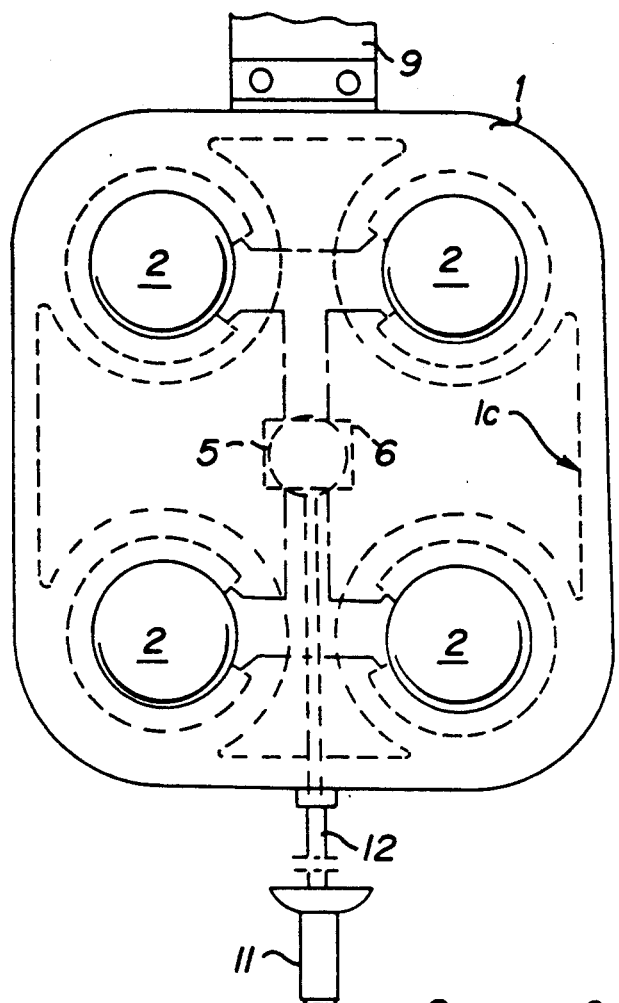
FIG. 2 is its front view.
Figure 3:
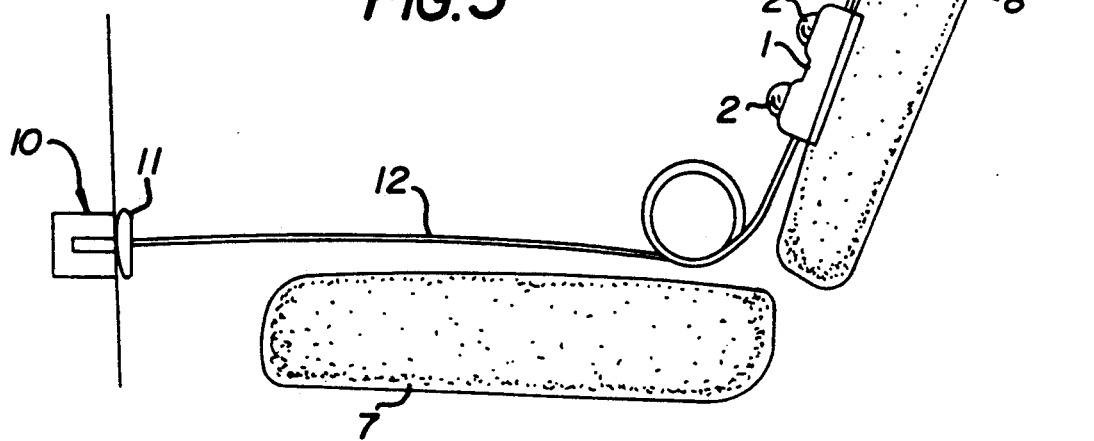
FIG. 3 is a schematic side view showing an example of its use.

FIG. 1 is a partially cut-away sectional view showing an embodiment of a massage machine of the invention, FIG. 2 is its front view, and FIG. 3 is a schematic side view showing an example of its use.

In FIG. 1, numeral 1 denotes a main body, 2 is a finger pressure ball, 3 is a magnet, 4 is a heater coil, 5 is a temperature sensor, and 6 is a pressure sensor.

The main body 1 is suspendably supported on a back rest 8 of an automobile seat 7 by means of a height-adjustable suspending member 9, and plural finger pressure ball bearing parts 1a disposed at proper intervals are provided on the front surface, and magnet mounting parts 1b are formed deep inside, and the entire structure is made of aluminum die-casting, or nonmagnetic material such as resin having adequate heat resistance and heat conducting property.

The suspending member 9 has a hook part 9a for stopping on the back rest 8 of the automobile seat 7 formed at its upper end, and the lower end is linked with the main body 1, and a length adjusting tool 9b is provided at a proper intermediate position, and the entire structure is shaped like a band or rope, and by adjusting this length adjusting tool, the suspending height position of the main body 1 is adjustable.

The length adjusting tool 9b may be either of stepped type or stepless type.

The finger pressure ball 2 is rotatably borne on each finger pressure ball bearing part 1a of the front surface of the main body 1, with its approximately half exposed and projected, and the entire piece is made of magnetic material such as steel ball, and its size is suited to press the painful spot of the human body, for example, 15.5 mm in diameter. The finger pressure ball bearing part 1a is approximately a semirecess spherical shape.

The magnet 3 is either a laminate of a plurality of thin pieces or a single thick piece disposed in the magnet installing part 1b in the deeper side of each finger pressure bearing part 1a, and it attracts and holds each finger pressure ball 2 rotatably in the bearing part 1a and also brings about a magnetic effect.

The heater coil 4 is embedded or properly fitted in the finger pressure ball bearing part 1a of the main body 1, opposite to each finger pressure ball 2, and is connected to the automobile power supply (not shown) by a cord 12 having a plug 11 through a power outlet such as cigarette lighter.

Wiring of the heater coil 4 may be either series or parallel as shown in FIG. 2.

As the heater coil 4, nichrome wire or other heating wire is used.

The temperature sensor 5 is built in a part of the main body 1, for example, in the excess wall removal vacancy 1c in the middle of the main body 1, or near the finger pressure ball bearing part 1a, and is designed to properly control the temperature of the heater coil (for example, 50° to 60° C.) by turning on or off, and is connected in series to the electric circuit of the heater coil 4. Meanwhile, a temperature setting knob is provided in the side wall of the main body 1, and the pressure sensor 6 is incorporated in a part of the main body 1, for example, in a cover plate 13 in the middle of the back side of the main body 1, and detecting the presence or absence of the pushing pressure of the user, the heater coil 4 is turned on or off, and it is connected in series to the electric circuit of the heater coil 4.

The pressure sensor 6 may be also installed in other position.

The pressure sensor 6 serves as the main switch of the electric circuit of the heater coil 4, and it is turned on when the pushing pressure by the user is sensed, and is turned off by delay timer or the like when the elimination of pushing pressure continues for a specific time at the time of alighting from the car or the like, thereby preventing chattering of electric contact.

The method of use and operation of the massage machine of the invention composed in this manner are explained below.

The hook part 9a of the suspending member 9 is stopped on the back rest 8 of the automobile seat 7 as shown in FIG. 3, and the main body 1 is set to the position abutting against the ailing spot, for example, the waist, by means of the length adjusting tool 9b, and the plug 11 of the cord 12 is inserted into the power outlet 10 of cigarette lighter or the like. The user sits on the seat 7 and presses the ailing spot to the main body 1. As a result, the pressure sensor 6 is turned on, and the heater coil 4 is energized to heat the finger pressure balls 2. As a result, the fatigued and contracted muscles in the ailing spot are stretched and massaged simultaneously by the finger pressure action and thermomassaging action. Not pressing the same spot, the user can slightly change the position vertically or laterally to press the peripheral muscles of the ailing spot to the finger pressure balls 2 to heat and massage the entire fatigued muscles, and moreover the magnetic effect by the magnets 3 act on the human body through the finger pressure balls 2 to promote the blood circulation, so that the muscular fatigue in the ailing spot may be promptly recovered by these synergistic effects. Since the finger pressure balls 2 are rotatably borne on the main body 1, the pressing position may be smoothly changed while pressing the body.

After massaging the waist, the back and shoulder may be similarly massaged by adjusting the length adjusting tool 9b.

The massage machine of the invention may be used also while running the car or while stopped by a red traffic light. It can be used not only by the driver but also by the passangers.

When not using, the current supply to the heater coil 4 is automatically cut off by pulling out the plug 11 of the cord, or when leaving the seat as detected by the pressure sensor 6 without pulling out.

The temperature of the heater coil 4 is properly controlled automatically by the temperature sensor 5, and will not be overheated.

The quantity and arrangement of finger pressure balls 2 are not limited to the illustrated example, and may be properly modified, and if holding of the finger pressure balls 2 on the main body is not enough with the magnetic attraction by the magnets 3 alone, it is also possible to hinge with retaining ring or fix with screw.

According to the invention, lumbago, stiff shoulder and the like can be easily healed and eliminated while seated in the driver's seat of an automobile for the athlete, professional driver and the like commuting to the destination by car or for the long-distance driver. Since the power source is taken from the power outlet of cigarette lighter or the like existing in the compartment of automobile, the power supply of the automobile can be easily used. In addition, since finger pressure balls are rotatably borne on the main body, the pressing position may be smoothly changed, and as the finger pressure balls are heated by heater coil, the finger pressure action and thermomassaging action may be provided simultaneously, and hence recovery from fatigue may be accelerated by heating, stretching and massaging the fatigued and contracted muscles, and at the same time the blood circulation is promoted by simultaneously applying the magnetic action, so that the muscular fatigue of the ailing spot may be recovered more promptly. It is also safe, not requiring any particular handling, and economical because the heating temperature of the heater coil is automatically and properly controlled by the temperature sensor, and the energization of the heater coil is controlled by on/off switching by the pressure sensor.

What is claimed is:

1. A massage machine for automobile comprising:
    a main body suspendaly supported on the back rest of an automobile seat by way of a height-adjustable suspending member,
    a plurality of ceramic finger pressure balls rotatably borne on the front surface of the main body in a projected state,
    magnets installed deeply inside of finger pressure ball bearing parts on the front surface of the main body corresponding to each finger pressure ball, attracting and holding each finger pressure ball rotatably about the bearing parts, and bringing about magnetic effects to each finger pressure ball,
    heater coils disposed at the finger pressure ball bearings parts of the main body corresponding to each finger pressure ball, and connected to an automobile power supply through a power supply outlet such as cigarette lighter,
    a temperature sensor incorporated in part of the main body to controlling the heater coils to a proper temperature by turning on and off, and
    a pressure sensor incorporated in part of the main body for controlling the heater coils by turning on and off by sensing the presence or absence of the pushing pressure of the user.

* * * * *